(12) United States Patent
Bates et al.

(10) Patent No.: US 6,468,291 B2
(45) Date of Patent: Oct. 22, 2002

(54) EMBOLI FILTRATION SYSTEM HAVING INTEGRAL STRUT ARRANGEMENT AND METHODS OF USE

(75) Inventors: Mark C. Bates, Charleston, WV (US); Michael Hogendijk, Palo Alto, CA (US)

(73) Assignee: Baff LLC, San Francisco, CA (US)

( * ) Notice: Subject to any disclaimer, the term of this patent is extended or adjusted under 35 U.S.C. 154(b) by 0 days.

(21) Appl. No.: 09/774,197

(22) Filed: Jan. 29, 2001

(65) Prior Publication Data

US 2001/0012951 A1 Aug. 9, 2001

Related U.S. Application Data

(63) Continuation-in-part of application No. 09/354,897, filed on Jul. 16, 1999, now Pat. No. 6,179,859.

(51) Int. Cl.[7] ............................................. A61M 29/00
(52) U.S. Cl. .................. 606/200; 606/159; 604/523; 604/164.13
(58) Field of Search .................. 606/200, 127, 606/114, 159, 110, 113, 167; 604/523, 164.13

(56) References Cited

U.S. PATENT DOCUMENTS

| | | | |
|---|---|---|---|
| 3,592,186 A | 7/1971 | Oster | 128/2 R |
| 3,683,904 A | 8/1972 | Forster | 128/127 |
| 3,952,747 A | 4/1976 | Kimmell, Jr. | 128/303 R |
| 3,996,938 A | 12/1976 | Clark, III | 128/348 |
| 4,046,150 A | 9/1977 | Schwartz et al. | 128/328 |
| 4,723,549 A | 2/1988 | Wholey et al. | 128/344 |
| 4,790,812 A | 12/1988 | Hawkins, Jr. et al. | 604/22 |
| 4,921,484 A | 5/1990 | Hillstead | 604/104 |
| 4,969,891 A | 11/1990 | Gewertz | 606/200 |
| 4,998,539 A | 3/1991 | Delsanti | 128/898 |
| 5,002,560 A | 3/1991 | Machold et al. | 606/198 |

(List continued on next page.)

FOREIGN PATENT DOCUMENTS

| | | |
|---|---|---|
| EP | 0 737 450 A1 | 10/1996 |
| WO | WO 96/01591 | 1/1996 |
| WO | WO 98/39053 | 9/1998 |

*Primary Examiner*—Pedro Philogene
(74) *Attorney, Agent, or Firm*—Fish & Neave; Nicola A. Pisano

(57) ABSTRACT

An emboli filtration apparatus is provided comprising a guide wire having a filter element captured thereon, so that the guide wire is free to rotate or translate while the filter element remains stationary. The apparatus allows for movement and rotation of the guide wire as devices are advanced over it to treat occlusive disease, substantially without dislodging the filter element.

19 Claims, 6 Drawing Sheets

U.S. PATENT DOCUMENTS

| | | | | |
|---|---|---|---|---|
| 5,011,488 | A | 4/1991 | Ginsburg | 606/159 |
| 5,071,407 | A | 12/1991 | Termin et al. | 604/104 |
| 5,102,415 | A | 4/1992 | Guenther et al. | 606/159 |
| 5,108,419 | A | 4/1992 | Reger et al. | 606/200 |
| 5,133,733 | A | 7/1992 | Rasmussen et al. | 606/200 |
| 5,329,942 | A | 7/1994 | Gunther et al. | 128/898 |
| 5,354,310 | A | 10/1994 | Garnic et al. | 606/198 |
| 5,370,657 | A | 12/1994 | Irie | 606/200 |
| 5,415,630 | A | 5/1995 | Gory et al. | 604/53 |
| 5,456,667 | A | 10/1995 | Ham et al. | 604/107 |
| 5,476,104 | A | 12/1995 | Sheahon | 128/757 |
| 5,658,296 | A | 8/1997 | Bates et al. | 606/127 |
| 5,662,671 | A | 9/1997 | Barbut et al. | 606/170 |
| 5,695,519 | A | 12/1997 | Summers et al. | 606/200 |
| 5,746,758 | A | 5/1998 | Nordgren et al. | 606/159 |
| 5,769,816 | A | 6/1998 | Barbut et al. | 604/96 |
| 5,779,716 | A | 7/1998 | Cano et al. | 606/114 |
| 5,792,300 | A | 8/1998 | Inderbitzen et al. | 156/244.13 |
| 5,795,322 | A | 8/1998 | Boudewijn | 604/22 |
| 5,810,874 | A | 9/1998 | Lefebvre | 606/200 |
| 5,814,064 | A | 9/1998 | Daniel et al. | 606/200 |
| 5,817,102 | A | 10/1998 | Johnson et al. | 606/108 |
| 5,827,324 | A | 10/1998 | Cassell et al. | 606/200 |
| 5,833,644 | A | 11/1998 | Zadno-Azizi et al. | 604/52 |
| 5,833,650 | A | 11/1998 | Imran | 604/53 |
| 5,846,260 | A | 12/1998 | Maahs | 606/200 |
| 5,876,367 | A | 3/1999 | Kaganov et al. | 604/8 |
| 5,893,867 | A | 4/1999 | Bagaoisan et al. | 606/198 |
| 5,895,399 | A | 4/1999 | Barbut et al. | 606/159 |
| 5,910,154 | A | 6/1999 | Tsugita et al. | 606/200 |
| 6,053,432 | A | 4/2000 | Daniel et al. | 606/200 |
| 6,059,814 | A * | 5/2000 | Ladd | |
| 6,129,739 | A | 10/2000 | Khosravi | 606/200 |
| 6,171,327 | B1 * | 1/2001 | Daniel et al. | |
| 6,179,861 | B1 | 1/2001 | Khosravi et al. | 606/200 |
| 6,277,138 | B1 * | 8/2001 | Levinson et al. | |
| 6,277,139 | B1 * | 8/2001 | Levinson et al. | |
| 6,336,934 | B1 | 1/2002 | Gilson et al. | |
| 2002/0002384 | A1 | 1/2002 | Gilson et al. | |

* cited by examiner

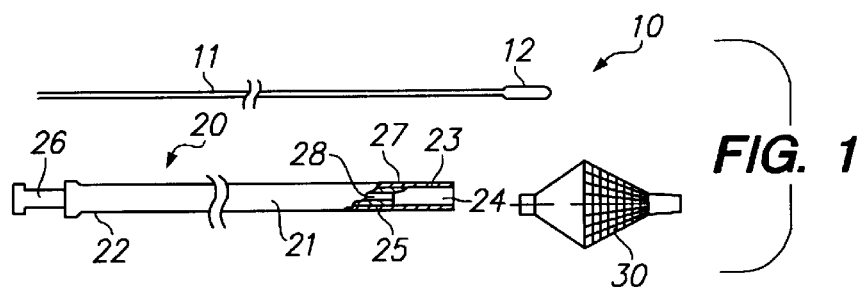
FIG. 1
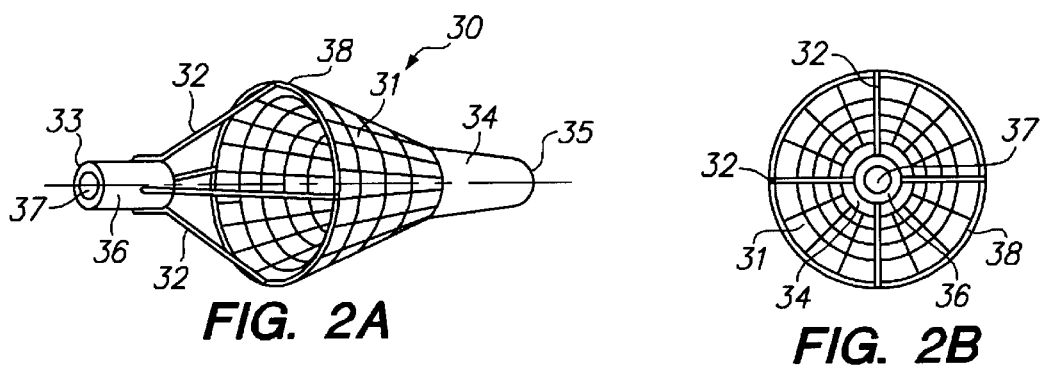
FIG. 2A
FIG. 2B
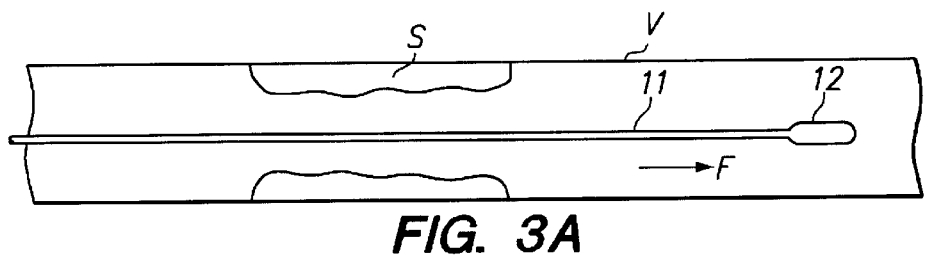
FIG. 3A
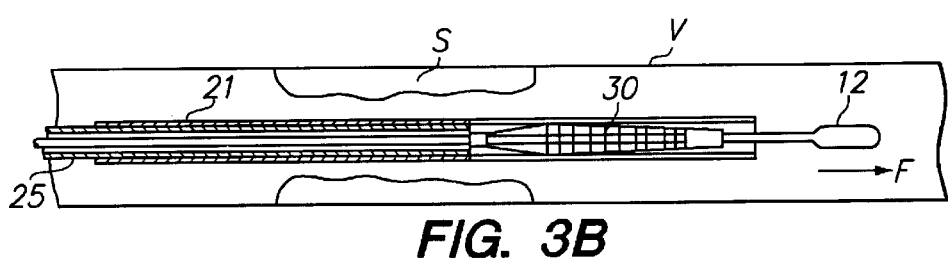
FIG. 3B
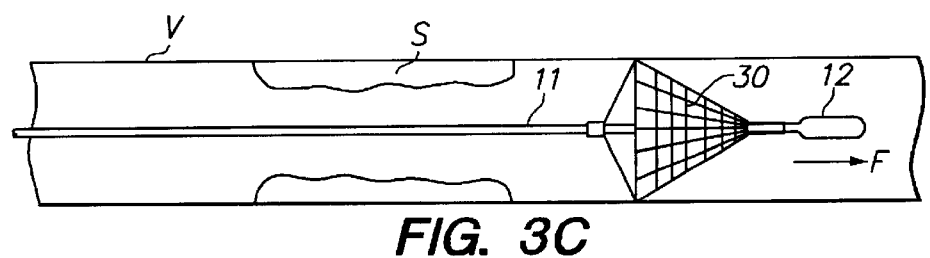
FIG. 3C

EMBOLI FILTRATION SYSTEM HAVING INTEGRAL STRUT ARRANGEMENT AND METHODS OF USE

REFERENCE TO RELATED APPLICATIONS

This application is a continuation-in-part application of U.S. patent application Ser. No. 09/354,897, filed Jul. 16, 1999, now U.S. Pat. No. 6,179,859.

FIELD OF THE INVENTION

The present invention relates apparatus and methods for removing emboli from the blood stream that are generated during treatment of vascular disease wherein a blood filter has a integral strut arrangement permitting reduced delivery profile and also enabling movement of a guide wire associated with the filter without displacing the filter.

BACKGROUND OF THE INVENTION

Atherosclerosis and other vascular occlusive diseases are becoming prevalent today in many developed countries. In such diseases, the flow areas of blood vessels become narrowed or occluded by the buildup of plaque on the walls of the vessels, leading to ischemia, and depending upon the location of the vessel, damage to the organ or limb. A number of surgical and percutaneous procedures have been developed for treating stenosis in the coronary arteries and carotid arteries, including endarterectomy, angioplasty, atherectomy and stenting.

One problem frequently encountered during such procedures is that pieces of plaque {"emboli"} often are dislodged from the stenosis or the vessel wall. Such emboli may travel into the smaller diameter regions of the vasculature, blocking blood vessels and causing ischemic injury. This problem is especially severe where the emboli are permitted to travel into the coronary arteries and cerebral arteries, and can result in infarction, stroke and even death.

Emboli filtration devices are known in which filter elements are deployed against the walls of a vessel distal to a stenosis. Such filters typically comprise a polymer or wire sac mounted on a distal region of a guide wire or angioplasty catheter, and permit blood to flow through the filter while trapping emboli. Once treatment of the stenosis is completed, the filter containing the captured emboli is contracted and withdrawn from the vessel.

For example, U.S. Pat. No. 5,814,064 to Daniel et al. describes an emboli capturing system having a radially expandable mesh filter disposed on the distal end of a guide wire. The filter is deployed distal to a region of stenosis, and any interventional devices, such as an angioplasty balloon or stent delivery system are advanced along the guide wire. The filter is designed to capture emboli generated during treatment of the stenosis while permitting blood to flow through the filter.

U.S. Pat. No. 4,723,549 to Wholey et al. describes an angioplasty catheter having a filter element disposed on its distal end. The filter is supported on a plurality of circumferential struts, and is expanded against the interior wall of a vessel, distal to a stenosis, by an inflation balloon. An angioplasty balloon is disposed on the catheter proximal of the filter for dilating the stenosis. The filter captures emboli dislodged during the dilatation procedure, and then is contracted and removed from the vessel with the angioplasty catheter.

A key disadvantage of previously known emboli filtration systems, such as described in the foregoing patents, is that the filters in those devices are fixedly attached to the guide wire or angioplasty catheter, respectively. If the catheter or guide wire is rotated, bumped or moved after the filter has been deployed, there is a substantial risk that filter will become temporarily dislodged or skewed, thereby permitting emboli to escape past the filter.

Moreover, movement of the deployed filter against the vessel wall also may damage the endothelium, and/or dislodge emboli distal to the filter. Such motion is especially likely to occur when other devices such as an angioplasty balloon catheter are deployed along the guide wire after the filter is deployed, as in the Daniels et al. patent.

In view of these disadvantages it would be desirable to provide emboli filtration apparatus and methods having a filter element that remains stationary once deployed.

It also would be desirable to provide emboli filtration apparatus and methods having a filter that may be deployed along a guide wire, but is configured so that subsequent displacements or rotation of the guide wire will not dislodge the filter.

It also would be desirable to provide emboli filtration apparatus and methods that self-center a filter element within a vessel, thereby preventing skewing or cocking of the filter element.

It further would be desirable to provide emboli filtration apparatus and methods that reduce the risk of emboli escaping from a filter element.

It still further would be desirable to provide emboli filtration apparatus and methods that reduce the risk of trauma to vessel endothelium resulting from movement transferred to the emboli filtration apparatus.

It yet further would be desirable to provide emboli filtration apparatus having a reduced delivery profile, thereby enabling the filter to use in smaller vessels and to negotiate more tortuous anatomy.

SUMMARY OF THE INVENTION

In view of the foregoing, it is an object of this invention to provide emboli filtration apparatus and methods having a filter element that remains stationary once deployed.

It is another object of the present invention to provide emboli filtration apparatus and methods having a filter that may be deployed along a guide wire, but is configured so that subsequent displacements or rotation of the guide wire will not dislodge the filter.

It is also an object of this invention to provide emboli filtration apparatus and methods that self-center a filter element within a vessel, thereby preventing skewing or cocking of the filter element.

It is also an object of this invention to provide emboli filtration apparatus and methods that reduce the risk of emboli escaping from a filter element.

It is a further object of the present invention to provide emboli filtration apparatus and methods that reduce the risk of trauma to vessel endothelium resulting from movement transferred to the emboli filtration apparatus.

It is a yet further object of the present invention to provide emboli filtration apparatus having a reduced delivery profile, thereby enabling the filter to use in smaller vessels and to negotiate more tortuous anatomy.

These and other objects of the present invention are accomplished by providing emboli filtration apparatus comprising a guide wire having a filter element captured thereon, so that the guide wire is free to rotate and/or translate while the filter element remains stationary. The apparatus thus allows for movement or rotation of the guide wire as devices are advanced over it to treat a stenosis, substantially without dislodging the filter element. Accordingly, the risk of permitting emboli to escape during temporary displacement or skewing of the filter element is reduced, as well as movement-induced trauma of the vessel endothelium.

In a preferred embodiment, the apparatus comprises a guide wire having a filter element captured for rotation and translation on a distal end thereof. The filter element preferably comprises a wire or polymer sac affixed to a plurality of self-expanding struts. The filter element has a contracted state, suitable for transluminal insertion disposed inside a retractable sheath, and a deployed state, wherein an outer perimeter of the filter element engages the walls of a vessel when the sheath is retracted proximally. In a more preferred embodiment, the self-expanding struts comprise portions of a unitary strut arrangement.

The filter element includes a proximal capture ring having a diameter which is larger than the diameter of the guide wire, but smaller than the diameter of the distal tip of the guide wire. The capture ring allows the guide wire to move freely relative to the filter element over a limited range, so that movement or rotation of the guide wire does not cause the filter to move or to scrape against the walls of the vessel. When it is desired to retract the filter element, the guide wire is pulled proximally so that the distal tip of the guide wire engages the capture ring and pulls the filter element back into a sheath to its contracted state.

Optionally, the filter element may include a cylindrical sleeve that ensures that the filter forms an adequate seal against the walls of the vessel in the deployed state, thus preventing bypass flow around the filter. The sleeve also assists in orienting the axis of the filter element parallel to the axis of the vessel. As a further option, the strut arrangement of the filter element may be deployed on a tubular member that facilitates movement of the filter and enables the use of an elongated filter sac. A retrieval catheter suitable for use with such embodiments is also provided.

Methods of using the apparatus of the present invention to remove emboli during a surgical or percutaneous transluminal procedure also are provided.

BRIEF DESCRIPTION OF THE DRAWINGS

Further features of the invention, its nature and various advantages will be apparent from the accompanying drawings and the following detailed description of the preferred embodiments, in which:

FIG. 1 is a side view of the components of a first embodiment of apparatus constructed in accordance with the principles of the present invention;

FIGS. 2A and 2B are, respectively, a perspective view and end view of the filter element of FIG. 1;

FIGS. 3A–3E are side sectional views showing deployment, use and removal of the apparatus of FIG. 1 in accordance with the methods of the present invention;

DETAILED DESCRIPTION OF THE INVENTION

Figure 3D:
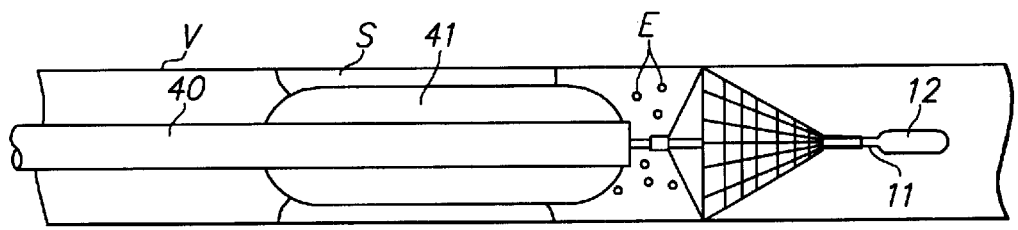
Figure 3E:
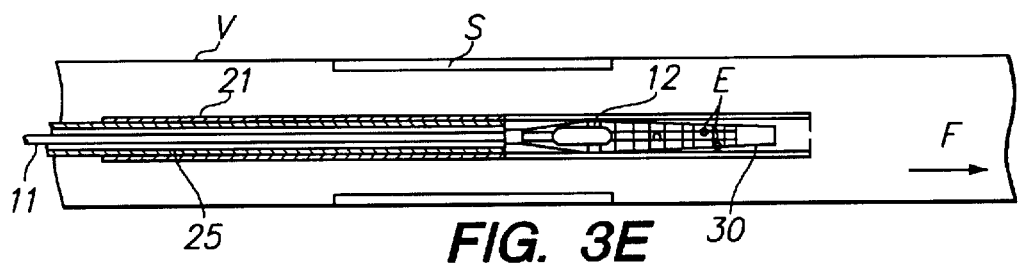

The present invention is directed to an emboli filtration system and methods that filter out emboli generated during surgical or percutaneous interventional procedures. In accordance with the principles of the present invention, a filter element is captured on a guide wire so that the guide wire is capable of rotation or translation, without disturbing the placement of the filter element. Because the filter element is captured on the guide wire, however, the filter element is readily removed by retracting the guide wire into a sheath.

Referring to FIG. 1, apparatus 10 of the present invention comprises guide wire 11, delivery sheath 20 and filter element 30.

In accordance with the principles of the present invention, guide wire 11 includes enlarged diameter distal region 12. Guide wire 11 may be constructed of material commonly used in guide wire construction, such as stainless steel or a high strength polymer. Distal region 12, which acts as a stop to limit travel of filter element 30 in the distal direction, comprises a soft metal or metal alloy coil or may be formed from a flexible polymer, such as polyethylene or nylon, molded onto the distal region of the guide wire. Alternatively, guide wire 11 and distal region 12 may comprise a mechanism, such as are known in the art, for steering distal region 12 through a patient's vasculature. Illustratively, guide wire may have a diameter of 0.018 inches (0.46 mm) and the diameter of distal region 12 may be 0.022 inches (0.56 mm).

Delivery sheath 20 comprises flexible catheter 21 having proximal end 22, distal end 23, and interior lumen 24. Push tube 25 is disposed within lumen 24, and includes proximal end 26, distal end 27 and guide wire lumen 28, to permit catheter 21 and push tube 25 to be advanced along guide wire 11. Proximal end 26 of push tube 25 extends through proximal end 22 of catheter 21, so that push tube 25 may be translated in the distal and proximal directions relative to catheter 21. Catheter 21 and push tube 25 preferably comprise flexible materials such as are commonly used in catheter construction, for example, polyethylene, polyurethane or nylon. Delivery sheath 20 preferably has an outer diameter of about 4 Fr.

Referring now also to FIGS. 2A and 2B, filter element 30 comprises funnel-shaped filter sac 31 coupled to a plurality of self-expanding struts 32 at proximal end 33 and soft elastomer cone 34 at distal end 35. Struts 32 are affixed to capture ring 36, and self-expand from a contracted state, when filter element is disposed in lumen 24 of catheter 21, and a deployed state, when filter element is ejected from delivery sheath 20. In the deployed state, struts 32 extend outward to urge the perimeter of sac 31 into engagement with the walls of a vessel.

Struts 32 may comprise a resilient metal or metal alloy, such as stainless steel or nickel-titanium, or a resilient polymer. It is expected that at least three struts 32 spaced equidistant apart around the perimeter of sac 31 should be employed to provide adequate expansion and control of the sac, although a greater number may be used. Alternatively, struts 31 may comprise flexible strands, and expansion of sac 31 may be accomplished by adding a flexible and resilient self-expanding nickel-titanium hoop along perimeter 38 of the sac.

Particulate matter, such as emboli, pass through struts 32 and are trapped against sac 31, which permits blood to pass freely through. The size of emboli trapped by sac 31 is determined by the pore size of the sac, and preferably is about 0.0012 inches (30 microns). Sac 31 may comprise a polymer sleeve affixed to struts 32 or a self-expanding wire mesh constructed from a resilient metal alloy, for example, nickel-titanium.

Capture ring 36 has bore 37 with an inner diameter greater than the diameter of guide wire 11, but smaller than the diameter of distal region 12. This allows guide wire 11 to be rotated or translated distally relative to filter element 30, without imposing a force on the filter element that might temporarily dislodge the filter element. Accordingly, various devices, such as angioplasty catheters, atherectomy devices or stent delivery systems may be exchanged on guide wire 11 without disturbing filter element 30 or causing it to scrape against the walls of the vessel. As will of course be understood, capture ring 36 need not be a tubular member, but may have any suitable shape that allows guide wire 11 to pass freely through it.

Elastomer cone 34 is coupled to the distal and of sac 31 and includes a tapered central lumen that permits guide wire 11 to freely pass through cone 34 with minimal clearance. Elastomer cone 34 preferably comprises a non-stick or slick surface, such as polytetrafluoroethylene, and is designed so that emboli trapped in sac 31 are prevented from passing out of the filter element through the space between guide wire 11 and the lumen of elastomer cone 34. Cone 34 is sufficiently soft and flexible so that its lumen can expand to permit distal region 12 of guide wire 12 to be pulled proximally through the cone, and then the lumen will seal itself to prevent emboli from escaping through the lumen, as described hereinafter.

Referring now to FIGS. 3A to 3E, methods of using the apparatus of FIG. 1 is described. In FIG. 3A, guide wire 11 first is percutaneously and transluminally inserted into vessel V, such as a coronary artery or common carotid artery, so that distal region 12 is disposed distal to stenosis S in the direction of blood flow (indicated by arrow F).

In FIG. 3B, delivery sheath 20 with filter element 30 loaded in lumen 24 in the contracted state is advanced along guide wire 11 until the filter element is disposed at a desired location distal to the stenosis, as determined, for example, by fluoroscopy. Proximal end 28 of push tube 25 is then held stationary while catheter 21 is retracted in the proximal direction.

As catheter 21 is retracted, struts 32 of filter element 30 expand outward to urge the perimeter of sac 31 into engagement with the walls of vessel V, as depicted in FIG. 3C. Delivery sheath 20 is then withdrawn proximally and removed from guide wire 11. Guide wire 11 then may be advanced distally, so that any incidental movement of the guide wire associated with exchanging interventional instruments along guide wire 11 will not cause distal region 12 to contact filter element 30.

In FIG. 3D, angioplasty catheter 40 is illustratively advanced along guide wire 11 until balloon 41 is disposed across the stenosis. Balloon 41 then is inflated and deflated for one or several cycles, as in conventional, to dilate and disrupt the plaque comprising stenosis S and increase the diameter of vessel V. During this dilatation procedure, particles of plaque or emboli E are generated. These emboli are carried by blood flow in direction F into sac 31 of filter element 30, where they become trapped.

Insertion and advancement of angioplasty catheter 40 along guide wire 11 may cause the guide wire to be translated over a short range or rotated. Because filter element 30 is not affixed to guide wire 11, however, such motion of the guide wire is not transferred to the filter element. Instead, filter element 30 remains stationary even though the guide wire rotates or translates relative to the filter element.

Once balloon 41 has dilated stenosis S, angioplasty catheter 40 is withdrawn along guide wire 11 while leaving the guide wire in place. If desired, a stent delivery system (not shown) may be advanced long guide wire 11 and one or more stents deployed across the dilated stenosis to retain the patency of the dilated vessel.

When treatment of the stenosis is completed, delivery sheath 20 (with push tube 25 removed) may again be advanced along guide wire 11 to a position just proximal of filter element 30. Guide wire 11 is then pulled proximally so that distal region passes through elastomer cone 34 and bears against capture ring 36. The lumen in cone 34 seals itself after distal region 12 passes through it so that emboli trapped in sac 31 do not escape through the lumen of cone 34.

When guide wire 11 is pulled further in the proximal direction, with catheter 21 held stationary, struts 32 are forced radially inward by distal edge of the catheter. This in turn causes sac 31 to disengage the vessel walls. As the guide wire continues to be pulled proximally, struts 32 cause sac 31 to collapse inward to its contracted position and the filter element is retracted into lumen 24 of catheter 21. Emboli E are trapped and retained in filter element 30 throughout treatment of the stenosis, and are withdrawn from the vessel when the filter element is retracted within catheter 21. Catheter 21 is then removed from the vessel.

Figure 4A:
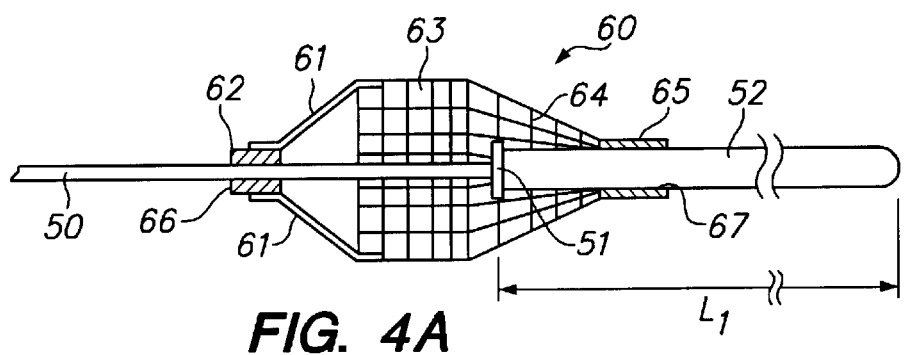
FIGS. 4A and 4B are, respectively, side sectional views of an alternative embodiment of the apparatus of the present invention in the deployed and contracted states.
Figure 4B:
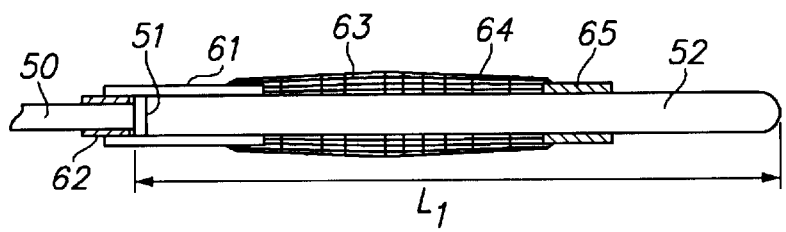

Referring now to FIGS. 4A and 4B, an alternative embodiment of the filter element and guide wire of the present invention is described. Guide wire 50 is similar in construction to guide wire 11 described with respect to FIG. 1, except that it includes flange 51 on enlarged diameter distal region 52 of guide wire 50, and enlarged distal region 52 has length $L_1$ that is longer than the length of the filter element 60 in the contracted state.

Distal region 52 may be formed from a malleable material, a coil spring, or a pliable thermoplastic material molded onto guide wire 50, and preferably is covered with a smooth hydrophillic coating to facilitate movement of filter element 60 as described hereinafter. Alternatively, guide wire 50 and distal region 52 may comprise a mechanism, such as are known in the art, for steering distal region 52 through a patient's vasculature. Distal region 52 also may comprise a radiopaque material or may include a radiopaque band 53 to assist in visualization and placement of the guide wire.

Filter element 60 comprises self-expanding struts 61 coupled to capture ring 62 and tubular sleeve 63. Sleeve 63 is affixed at its distal end to funnel-shaped filter sac 64, which in turn is coupled to distal ring 65. Capture ring 62 has bore 66 with an inner diameter larger than the diameter of guide wire 50, but smaller than the diameter of distal region 52. Accordingly, guide wire 50 may freely translate and rotate through bore 66 of capture ring 62 while the filter element remains stationary. Distal ring 65 has bore 67 with a diameter slightly larger than the diameter of distal region 52. This enables distal ring 65 to slide or rotate freely over distal region 52, but with minimal clearance for emboli to escape from sac 64 through the annulus between distal ring 65 and distal region 52. Distal region 52 includes flange 51, which has a diameter that is larger than the diameter of bore 66 of capture ring 62. Thus, filter element 60 is captured on guide wire 50 proximally by distal ring 65 abutting against flange 51, and distally by capture ring 62 abutting against flange 51.

Sleeve 63 and sac 64 filter blood passing through the vessel, and have a pore size selected to filter out particles having a diameter greater than 0.0012 inches (30 microns). Sleeve 63 and sac 64 preferably comprise a flexible woven metal alloy, polymer tube, or perforated fabric, and are expanded to the deployed state by struts 61. Advantageously, sleeve 63 is designed so that its perimeter conforms to the inner diameter of the vessel to seal against bypass flow, even in curved vessels. In addition, sleeve 63 tends to prevent skewing of the filter element and ensures that the filter is properly oriented parallel to the axis of the vessel when the filter element is deployed.

Filter element 60 is suitable for delivery percutaneously and transluminally to a desired location in a vessel using delivery sheath 20 of FIG. 1. In particular, struts 61 may be radially compressed to collapse sleeve 63 and sac 64, thereby permitting these the filter element to be loaded into lumen 24 of catheter 21 so that capture ring 62 abuts against distal end 27 of push tube 25.

Deployment of filter element 60 is similar to the method described with respect to FIGS. 3B and 3C. Specifically, delivery sheath 20 is advanced through a vessel with distal region 52 extending beyond distal end 23 of catheter 21. Once the distal region has crossed the stenosis, as confirmed by fluoroscopy, push tube 25 is held place and catheter 21 is retracted proximally. Alternatively, push tube 25 may be omitted and guide wire 50 may be held stationary with filter element 60 held in position by flange 51. Retraction of catheter 21 uncovers filter element 60, allowing struts 61 to expand outward and urge the perimeter of sleeve 63 and sac 64 into engagement with the walls of the vessel.

Delivery sheath 20 then is removed, and one of more interventional devices may be serially employed on guide wire 50. As for the embodiment of FIG. 1, motion imparted to the guide wire during exchange of instruments along the guide wire causes the guide wire to slide through filter element 60 without causing skewing or displacement of the filter element. Advantageously, this prevents emboli from escaping sac 64 or damage to the endothelium caused by scraping of the filter element.

Once treatment of the stenosis is completed, the treatment device (e.g., angioplasty catheter, etc.) is removed, and delivery sheath 20 is again advanced along guide wire 50. When distal end 23 of catheter 21 is disposed adjacent to capture ring 62, guide wire 50 is pulled proximally. As a result of this motion, distal region passes through filter element 60 until flange 51 abuts against capture ring 62. Further proximal movement of guide wire 50 causes struts 61 to be urged inward, collapsing sleeve 63 and sac 64 so that they can be drawn into lumen 24 of catheter 21.

Unlike the embodiment of FIG. 1, where the distal region passes through cone 34, length $L_1$ is sufficiently long so that distal ring 65 is still disposed over the enlarged diameter of distal region 51 when the filter element is in the contracted state. Accordingly, when filter element 60 is contracted for removal, emboli cannot escape through bore 67 of distal ring 65, since the bore continues to be substantially blocked by distal region 52 of guide wire 50. Delivery sheath 20, guide wire 50 and filter element 60 are then removed from the vessel with any emboli trapped within the contracted filter element.

In a preferred embodiment of the apparatus of FIGS. 4, guide wire 50 has a suitable length for transluminal percutaneous applications and a diameter in a range of 0.006 and 0.025 inches, and more preferably 0.012 inches. Distal region 52 of guide wire 50 has a diameter larger than the diameter of guide wire 50, and preferably in a range of 0.010 and 0.038 inches, more preferably 0.018 inches.

While filter element 60 may any length suitable for an intended application, in one preferred embodiment, filter element 60 has a deployed length of 3.5 cm and a maximum deployed diameter of 12 mm. For this embodiment, length $L_1$ of distal region 52 preferably is 5.0 cm. For a guide wire having a diameter of 0.012 inches and proximal ring and distal region having equal diameters of 0.018 inches, capture ring 62 preferably has an inner diameter of 0.014 inches and an outer diameter of 0.018 inches. In this case distal ring 65 preferably has an inner diameter of 0.0181 inches and an outer diameter of 0.024 inches.

Figure 5A:
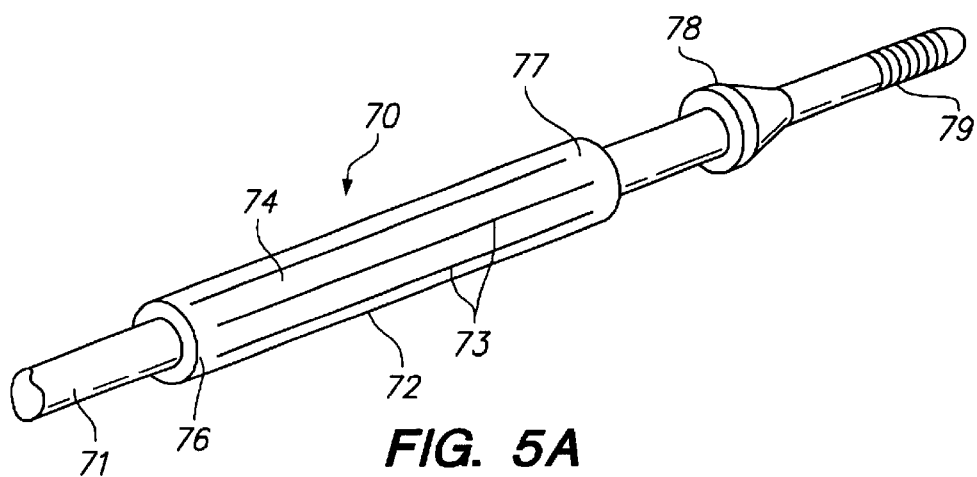
FIGS. 5A–5C are, respectively, perspective and side views of an alternative embodiment of the apparatus of the present invention.
Figure 5B:
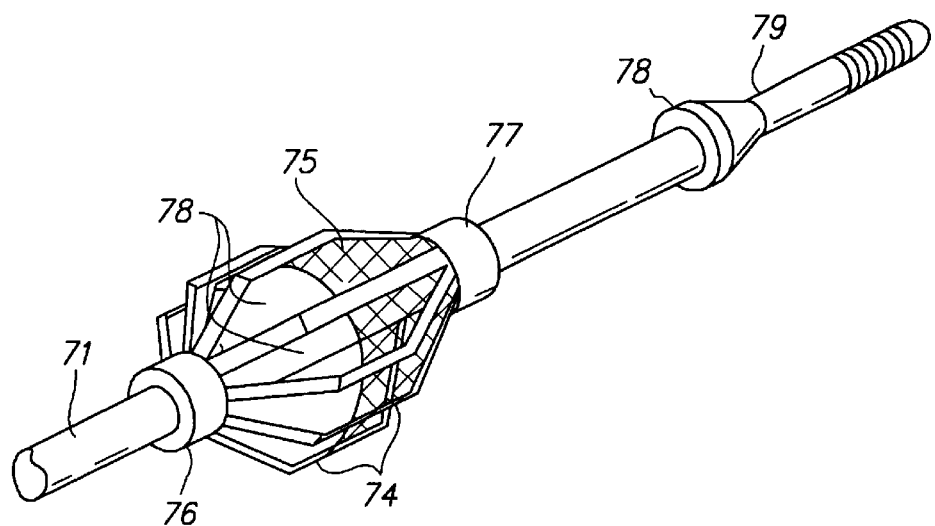
Figure 5C:
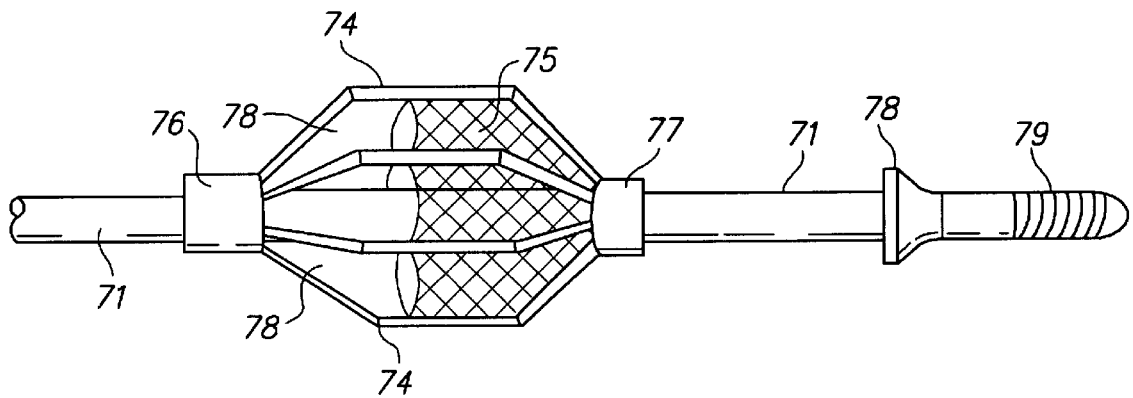

Referring now to FIGS. 5A–5C, another alternative embodiment of the present invention is described in which the capture ring, self-expanding struts and distal ring of the apparatus of FIGS. 4 are integrally formed from a slit tubular segment. In FIGS. 5A–5C, filter element 70 is disposed on guide wire 71 and comprises tubular segment 72 having a plurality of through-wall longitudinal slits 73 defining struts 74. Blood permeable sac 75 is affixed to the distal portion of the interior surface of tubular segment 72, and filters blood passing therethrough when filter element 70 is deployed.

In a preferred embodiment, tubular segment 72 comprises a shape-memory alloy, such as nitinol, which has been processed to assume an expanded, deployed state when ejected from a delivery sheath. As depicted in FIGS. 5A–5C, tubular segment illustratively includes a plurality of longitudinal slits disposed circumferentially around tubular segment 71 to define a plurality of self-expanding struts 74. The non-slitted proximal portion 76 and distal portion 77 form capture rings that correspond to capture ring 62 and distal ring 65 of the embodiment of FIGS. 4. Illustratively, tubular segment 72 includes nine slits defining ten self-expanding struts.

Distal end 79 of guide wire 71 preferably includes a floppy or bendable tip, as is per se known in the art. In addition, distal stop 78 may be tapered where it joins guide wire 71 so that the distal stop serves as a nosecone, thereby facilitating passage of the guide wire and filter element through a vessel.

When filter element 70 is unconstrained by a delivery sheath, i.e., ejected from a delivery sheath, struts 74 expand outwardly and the filter element foreshortens. As struts 74 expand outwardly, they carry sac 75 into apposition with the vessel wall, and create passages 78 that permit blood to flow into the sac, thereby filtering emboli from the blood stream. Sac 75 preferably comprises a biocompatible material that provides emboli filtration, as in the foregoing embodiments. In addition, sac 75 may comprise an elastomeric material that stretches to accommodate the degree of expansion of struts 74, thereby permitting filter element 71 to be used in a range of vessel sizes while reducing the risk of bypass flow caused by incomplete apposition of the sac with the vessel wall.

In accordance with the principles of the present invention, proximal portion 76 and distal portion 77 permit guide wire 71 to freely translate and rotate relative to filter element 70, without disturbing the location of filter element within the vessel. Accordingly, guide wire 71 includes distal stop 78 against which capture ring 77 abuts to limit distal movement of the filter along guide wire 71, and optionally may include a proximal stop (not shown) against which proximal capture ring 76 may abut to limit proximal movement. Filter element thus may be inserted along a previously-delivered guide wire, as depicted in FIGS. 3, or may be delivered captured between proximal and distal stops and inserted with the guide wire itself, as described hereinafter.

Advantageously, because struts 74 and capture rings 76 and 77 may be integrally formed from a single tubular segment, the overall diameter of the filter element in the contracted delivery diameter may be smaller that obtainable using separately-formed struts. Also, because a portion of the filter struts 74 lie flush against the vessel wall when the filter element is deployed, the struts facilitate self-centering and alignment of the filter element within a vessel, and provide stability and good apposition of the sac to the vessel wall. In addition, the number of separate parts employed in the design, and thus the assembly time and manufacturing cost of the device, are substantially reduced.

While the embodiment of FIGS. 5 illustratively includes nine slits 73 defining ten struts 74, more or less slits (and thus struts) may used, as will be apparent to one of ordinary skill in the art. Moreover, while in the depicted embodiment the longitudinal slits are spaced equi-distant apart around the circumference of tubular segment 72 to form equal-width struts, other arrangements may be desirable for specific applications.

Referring now to FIGS. 6 and 7, a further alternative embodiment of the embolic filtration apparatus of the present invention is described. Filter element 80 is similar in construction to the embodiment of FIGS. 5, and also employs tubular segment 81 having a plurality of longitudinally-extending circumferential slits 82 that define self-expanding struts 83. Tubular segment 81 is disposed on tube 85, which preferably is captured on guide wire 86 between optional proximal stop 87 and distal stop 88. Blood permeable sac 89 is affixed to the exterior surface of struts 83 at proximal end 90 and to tube 85 at distal end 91.

Figure 6A:
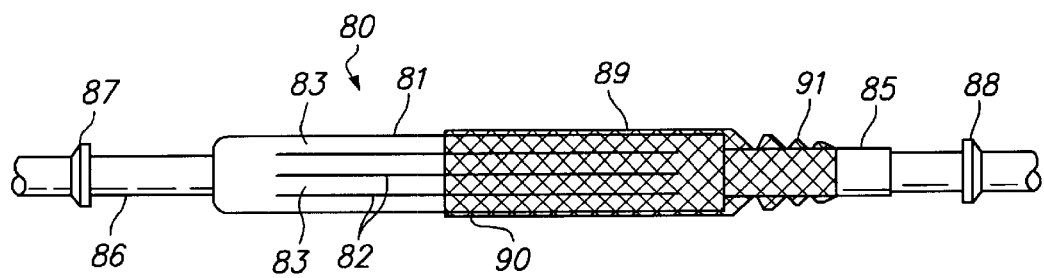
FIGS. 6A and 6B are side views of a further alternative embodiment of a filter constructed in accordance with the present invention in a contracted delivery state and deployed state.
Figure 6B:
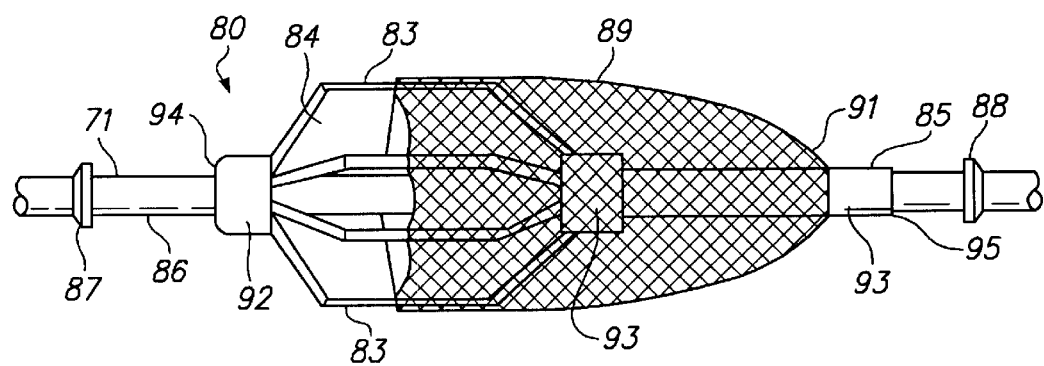

FIG. 6A depicts filter element 80 in a contracted delivery state, as it might be disposed and constrained within a delivery sheath, while FIG. 6B shows filter element 80 deployed. Tubular segment 81 is processed (e.g., heat treated) so that, when unconstrained, struts 83 of deploy outwardly creating openings 84 through which emboli and debris from a vascular procedure enter blood permeable sac 89. As will of course be understood, the distal end of guide wire 86 may terminate with a floppy tip, and tubular segment may include any number of longitudinal slits (and thus struts) as may be desired for a particular application.

Figure 7A:
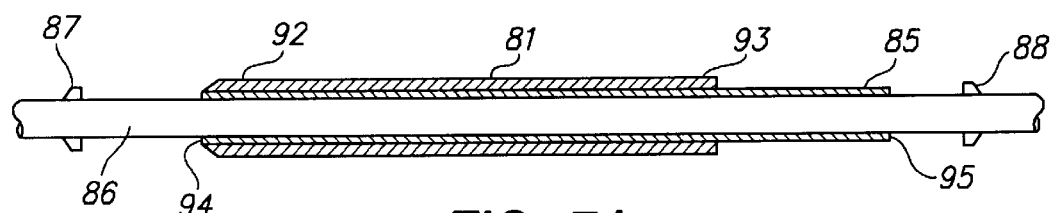
FIGS. 7A and 7B are side sectional views of the filter strut component of the apparatus of FIGS. 6.
Figure 7B:
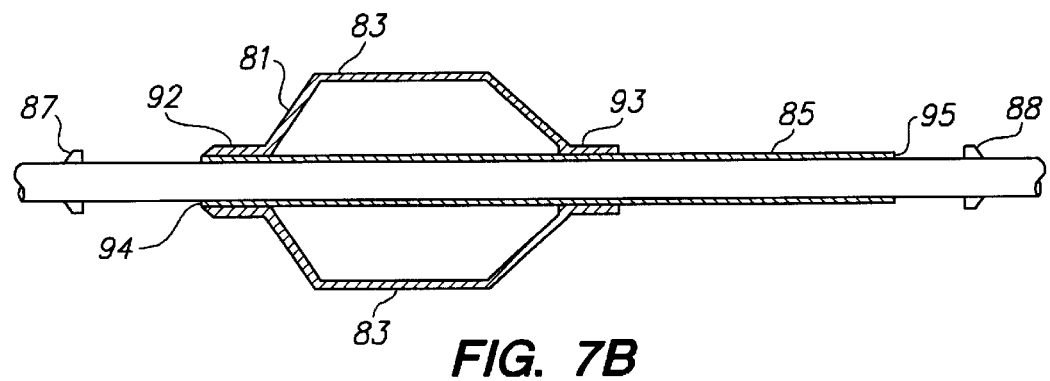

As depicted more clearly in FIGS. 7A and 7B, the non-slitted proximal portion of tubular segment 81 forms proximal collar 92, and is affixed to tube 85. The non-slitted distal portion of tubular segment 81 forms collar 93, and is slidingly disposed on tube 85, so that the collar 93 slides along tube 83 towards collar 92 when the filter element is deployed. Like the capture rings of the previously described embodiments, tube 85 serves as a linear bearing for filter element 80.

Tube 85 also corresponds to the capture ring of previous embodiments, because its proximal endface 94 abuts against proximal stop 87 to limit distally-directed motion of guide wire 86 while its distal endface 95 abuts against distal stop 88 to limit proximally-directed motion of guide wire 86. Tube 85 preferably comprises a flexible material, such as polyimide or other plastic, and more preferably is lubricious or may include an internal coating of a lubricious material, such as PTFE, to facilitate movement of guide wire 86 relative to tube 85.

In accordance with the principles of the present invention, guide wire 86 is capable of rotation and/or a limited range of translation relative to tube 85, and thus filter element 80, without disturbing the position of the filter. Advantageously, arrangement of tubular segment 81 and sac 89 on tube 85 permits the filter sac to be elongated compared to the embodiment of FIGS. 5. This in turn provides greater surface area for the filter, and reduces the risk that the pores of sac 89 may become clogged if unexpectedly large amounts of emboli or other debris are captured by the filter. Filter element 80 of FIGS. 6 and 7 therefore provides structural simplicity, with enhanced filtration capacity.

Figure 8A:
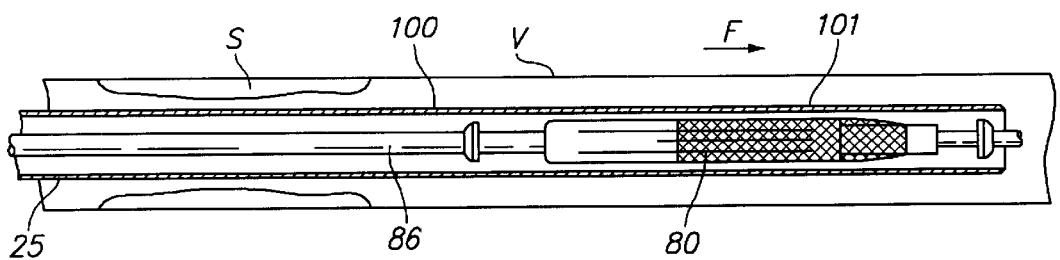
FIGS. 8A–8D are, respectively, side sectional and side view of the apparatus of FIGS. 6 being use in conjunction with an angioplasty balloon to treat vascular disease.

Referring now to FIGS. 8A to 8D, methods of using the apparatus of FIGS. 6 is described. In FIG. 8A, delivery sheath 100 enclosing guide wire 86 and filter element 80 is percutaneously and transluminally inserted into vessel V, such as a coronary artery or common carotid artery, so that distal region 101 is disposed distal to stenosis S in the direction of blood flow (indicated by arrow F). A floppy tip disposed on the distal end of guide wire 86 extends (to the right in FIG. 8A) pass the location the filter element and is used to traverse the stenosis.

Figure 8B:
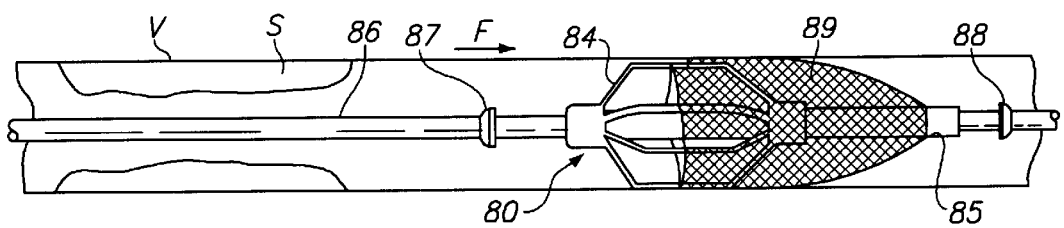

In FIG. 8B, once the position of the filter element is disposed at a desired location distal to the stenosis, as determined, for example, by fluoroscopy, delivery sheath 100 is retracted while guide wire 86 is held stationary. Because filter element 80 can only move in the proximal direction until it abuts against proximal stop 87, further retraction of delivery sheath 100 will cause filter element 80 to exit the distal end of the catheter.

As soon as catheter 100 is removed, struts 83 of filter element 80 expand outward to urge the perimeter of sac 89 into engagement with the walls of vessel V, as depicted in FIG. 8B. Delivery sheath 100 then is withdrawn proximally and removed from guide wire 86. Guide wire 86 then may be retracted a short distance proximally so that any incidental movement of the guide wire associated with exchanging interventional instruments along the guide wire will not cause proximal stop 87 to contact or disturb the position of filter element 80.

Figure 8C:
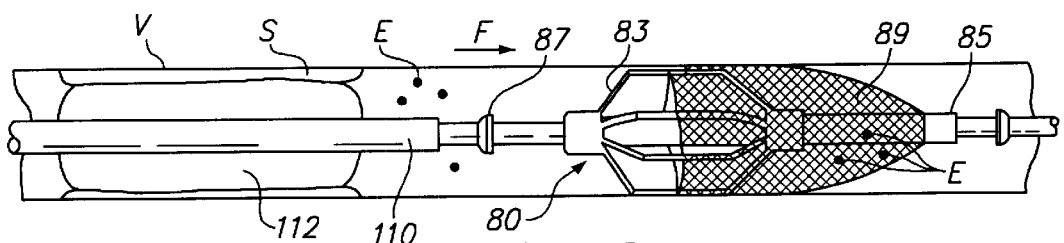
Figure 8D:
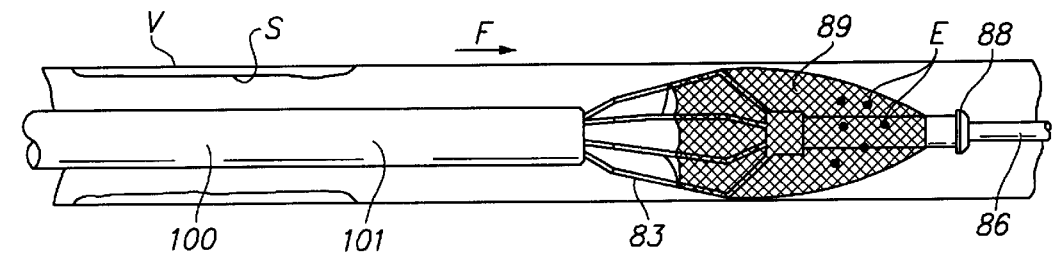

In FIG. 8C, angioplasty catheter 110 is illustratively advanced along guide wire 86 until balloon 112 is disposed across the stenosis. Balloon 112 then is inflated and deflated for one or several cycles, as in conventional, to dilate and disrupt the plaque comprising stenosis S and increase the diameter of vessel V. During this dilatation procedure, particles of plaque or emboli E are generated. These emboli are carried by blood flow in direction F into sac 89 of filter element 80, where they become trapped.

Insertion and advancement of angioplasty catheter 100 along guide wire 86 may cause the guide wire to be translated over a short range or rotated. Because filter element 80 is not affixed to guide wire 86, however, such motion of the guide wire is not transferred to the filter element. Instead, filter element 80 remains stationary even though the guide wire rotates or translates relative to the filter element.

Once balloon 112 has dilated stenosis S, angioplasty catheter 110 is withdrawn along guide wire 86 while leaving the guide wire in place. If desired, a stent delivery system (not shown) may be advanced along guide wire 86 and one or more stents deployed across the dilated stenosis to retain the patency of the dilated vessel.

When treatment of the stenosis is completed, delivery sheath 100 may again be advanced along guide wire 86 to a position just proximal of filter element 80. Guide wire 86 then held stationary while the distal region of sheath 100 contacts and translates the filter element slightly distally until it abuts against distal stop 88. As the sheath is advanced further in the distal direction, struts 83 and sac 89 collapse and enter into distal end 101 of the delivery sheath. Because sac 89 is elongated, closing of struts 83 closes the mouth of the sac, and prevents emboli trapped in sac 89 from escaping into the bloodstream.

Once filter element 80 is collapsed to its contracted position and retracted within the lumen of delivery sheath 100, the delivery sheath, guide wire and filter element are removed from the vessel. Emboli E are trapped and retained in filter element 80 throughout treatment of the stenosis, and are withdrawn from the vessel when the filter element is retracted within sheath 100.

Figure 9:
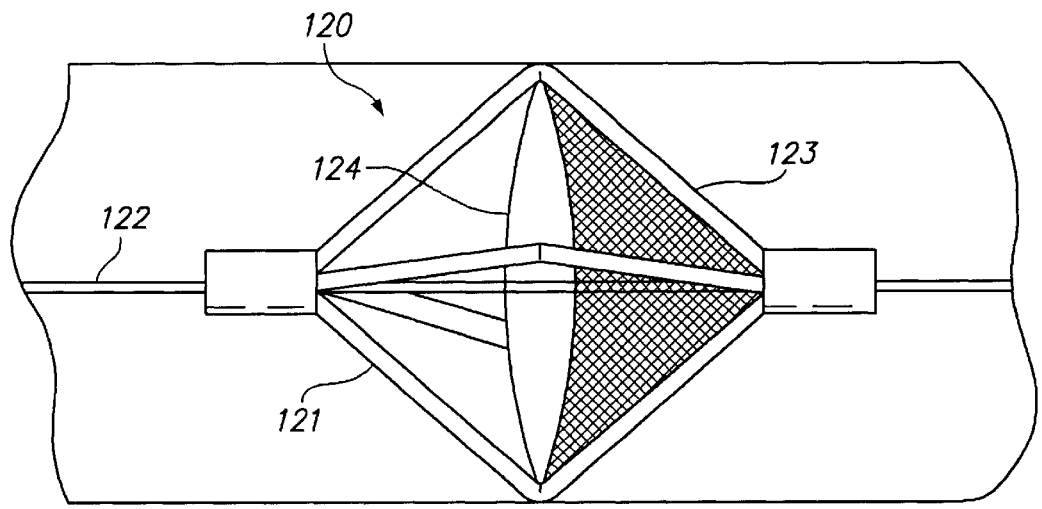
FIG. 9 is a side view of a further alternative embodiment of the apparatus of the present invention in the deployed state.

With respect to FIG. 9, a further alternative embodiment of an embolic filtration apparatus of the present invention is described. Filter element 120 comprises tubular segment 121 disposed on guide wire 122, and comprises a slit tubular segment as described with respect to the embodiments of FIGS. 5–8. Tubular segment 121 is processed so that struts 123 do not have a portion that lies flush against a vessel wall, as may be desirable for some situations, e.g., for short vessel lengths.

As for the previous embodiments, struts 123 are self-expanding, and form a basket shape when unconstrained. Blood permeable sac 124 is affixed to the interior surfaces of struts 123 to span the vessel cross-section when the filter element is deployed. Sac 124 may comprise a microaggregate blood transfusion filter such as PALL SQ40SK, with a pore size of about 80–200 microns, or a woven material.

Figure 10A:
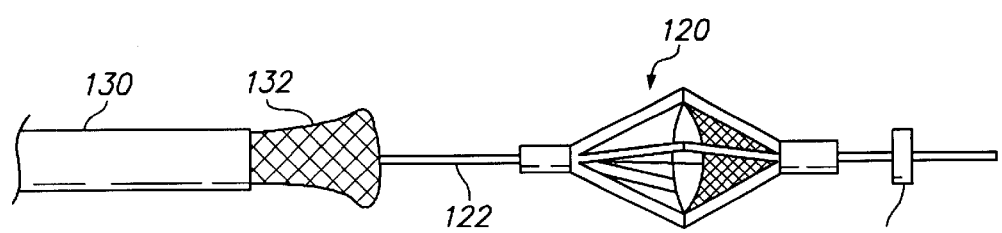
FIGS. 10A and 10B are side views illustrating use of a retrieval catheter suitable for use in recovering the filter element of FIG. 9.
Figure 10B:
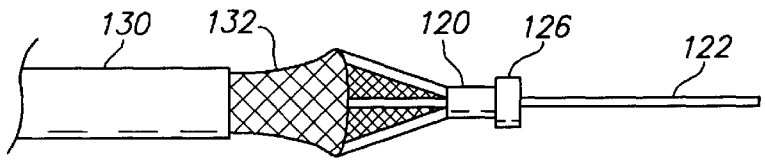

Referring now to FIGS. 10A and 10B, use of filter element 120 with a retrieval catheter constructed in accordance with another aspect of the present invention is described. In FIG. 10A, filter element 120 is shown after completion of an interventional procedure, such as angioplasty, and is disposed on guide wire 122 between retrieval catheter 130 that includes recovery sock 132 and distal stop 126. Recovery sock 132 comprises a material that is permeable to blood flow, but that has a pore size sufficiently small to prevent emboli from passing through it.

As shown in FIG. 10B, with guide wire 122 first is withdrawn proximally (to the left in FIG. 10B) until distal stop 126 contacts the distal end of filter element 120. With guide wire 122 held stationary, retrieval catheter 130 is advanced distally until sock 132 engages and covers the proximal end of filter element 120. As retrieval catheter 130 is advanced further in the distal direction, struts 123 and sac 124 of filter element 120 collapse and are drawn into the lumen of the retrieval catheter. Recovery sock 132 thereby ensures that emboli captured in sac 124 do not escape into the blood stream during retrieval of filter element 120.

Figure 11:
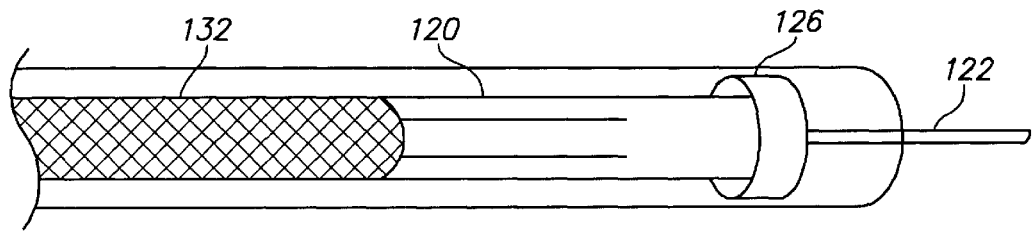
FIG. 11 is a side view showing the filter element and retrieval catheter of FIGS. 10 in condition to be withdrawn from a vessel.

By advancing retrieval sheath 130 along guide wire 120 with the distal end of filter element 120 abutted against distal stop 126, struts 123 are caused to collapse and enter the lumen of the retrieval catheter. Recovery sock 132 preferably contracts and continues to cover struts 123 as the filter element is collapsed, resulting in situation depicted in FIG. 11. Filter element 120, guide wire 122 and retrieval catheter 130 now may be easily withdrawn from the vessel.

Figure 12:
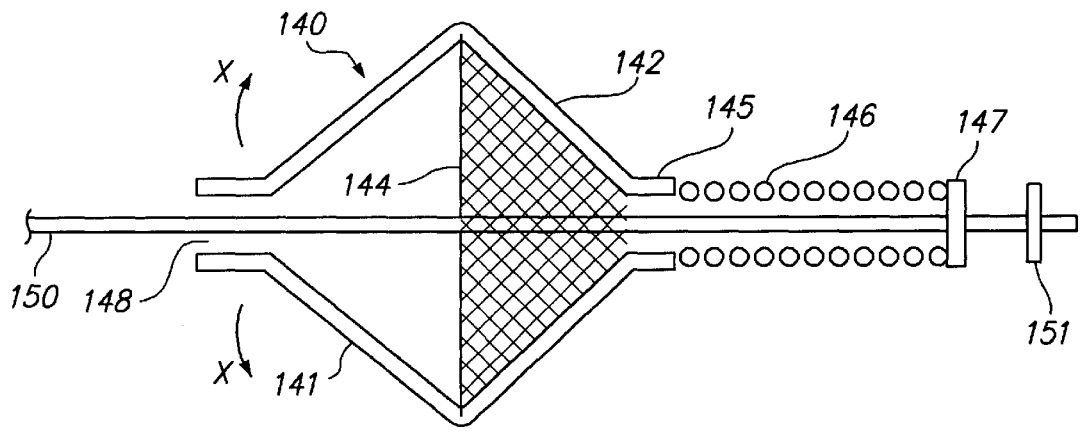
FIG. 12 is a side sectional view of yet another filter element constructed in accordance with the present invention that includes a coil to accommodate lateral displacement of the filter element.

Referring to FIG. 12, yet another alternative embodiment of the embolic filtration apparatus of the present invention is described. In the embodiment of FIG. 12, filter element 140 is similar to filter element 120 of FIG. 9, and includes slit tubular segment 141 forming struts 142 which form a basket and lood permeable sac 144 affixed to the interior surface of the struts. Tubular segment 141 is coupled at distal end 145 to flexible coil 146. Coil 146 preferably comprises a flexible spiral coil, and is in turn connected to linear bearing 147 that is slidingly disposed on guide wire 150.

Guide wire 150 preferably has a smaller diameter than the diameter of tubular segment 141, and includes distal stop 151 against which linear bearing 147 abuts to limit distally-directed travel of filter element 140. Guide wire 150 extends through the interior lumen 148 of tubular segment 141 and interior lumen of coil 146 and linear bearing 147 to enable filter element 140 to rotate and/or translate freely relative to guide wire 150.

In accordance with another aspect of the present invention, the clearance between the guide wire and interior surface of tubular segment 141, in combination with the presence of coil 146, permits the proximal end of the filter to rotate relative to its distal end. This arrangement permits the filter element to accommodate some lateral displacement of the filter element from a position concentric with the guide wire, as indicated by the arrows X in FIG. 12.

Moreover, depending upon the stiffness of coil 146, the filter may also undergo a degree of lateral deflection (without end-to-end rotation) from the longitudinal axis of guide wire 150. However, because emboli may pass through lumen 148 between guide wire 150 and the distal end of tubular segment 141 into the lumen of coil 146, the spirals of coil 146 preferably are tightly packed so that emboli cannot escape through filter element 140 via coil 146.

One skilled in the art will appreciate that the present invention may be practiced by other than the described embodiments, which are presented for purposes of illustration and not limitation. It is intended that the present application cover such variations or modifications as may be apparent from the described embodiment as may fall within the scope of the appended claims.

What is claimed is:

1. Apparatus for filtering emboli from blood flowing through a vessel, the apparatus comprising:
   a guide wire having a distal region and a distal stop disposed on the distal region;
   a tubular segment disposed on the distal region of the guide wire proximal to the distal stop, the tubular segment having a circumference and a plurality of longitudinally-extending through-wall slits disposed around the circumference, the longitudinally-extending through-wall slits defining a plurality of self-expanding struts; and
   a filter sac disposed on the struts of the tubular segment.

2. The apparatus of claim 1 wherein the guide wire further includes a proximal stop disposed on the guide wire proximal to the tubular segment.

3. The apparatus of claim 1 further comprising a tube interposed between the tubular segment and the guide wire, the filter sac coupled to a distal end of the tube.

4. The apparatus of claim 1 further comprising a retrieval catheter having a distal end and a recovery sock coupled to the distal end, wherein the recovery sock prevents emboli captured by the fileter sac from escaping into the blood when the tubular segment is collapsed for removal.

5. The apparatus of claim 1 wherein each one of the plurality of self-expanding struts includes a portion that lies flush against the vessel when the apparatus is deployed.

6. The apparatus of claim 1 wherein the filter sac is affixed to an interior surface of the plurality of self-expanding struts.

7. The apparatus of claim 1 wherein the filter sac is at least partially affixed to an exterior surface of the plurality of self-expanding struts.

8. The apparatus of claim 1 further comprising:
   a linear bearing disposed on the guide wire proximal to the distal stop; and
   a flexible coil coupled between the linear bearing and a distal end of the tubular segment.

9. The apparatus of claim 8 wherein the coil comprises a plurality of adjacent turns, the plurality of adjacent turns being spaced sufficiently close to one another enough that emboli cannot pass therebetween.

10. Apparatus for filtering emboli from blood flowing through a vessel, the apparatus comprising:
    a guide wire having a distal region;
    a filter element disposed for rotation on the distal region of the guide wire, the filter element comprising a self-expanding strut and a filter sac connected to the self-expanding strut; and
    a distal stop disposed on the distal region distal to the filter element, the distal stop limiting distal translation of the filter element on the guide wire.

11. The apparatus of claim 10 wherein, when the filter sac is deployed in the vessel, rotation of the guide wire does not displace the filter element.

12. The apparatus of claim 10 further comprising a proximal stop disposed on the guide wire proximal to the filter element.

13. The apparatus of claim 12 wherein the filter element is disposed for sliding translation on the guide wire between the proximal stop and the distal stop.

14. The apparatus of claim 10 wherein the filter element further comprises a flexible tube interposed between the guide wire and the self-expanding strut, a distal end of the filter sac being coupled to the flexible tube.

15. The apparatus of claim 10 wherein the filter element comprises a tubular segment having a circumference and a plurality of longitudinally-extending through-wall slits disposed around the circumference, the longitudinally-extending through-wall slits defining the self-expanding strut.

16. The apparatus of claim 10 further comprising:
    a linear bearing disposed on the guide wire proximal to the distal stop; and
    a flexible coil coupled between the linear bearing and a distal end of the filter element.

17. A method of filtering emboli from blood flowing through a vessel, the method comprising:
    providing a guide wire having a distal region including a distal stop, and a filter element disposed for translation on the guide wire proximal to the distal stop, the filter element comprising a plurality of self-expanding struts having a filter sac affixed thereto;
    transluminally inserting the guide wire and filter element into a vessel;
    deploying the filter element so that the struts and filter sac expand to engage a wall of the vessel, the filter sac filtering emboli out of blood flowing through the vessel;
    advancing a treatment device along the guide wire to treat a portion of the vessel proximal to the location of the filter element, rotation or distal translation of the guide wire relative to the filter element imparted by the treatment device not displacing the filter element.

18. The method of claim 17 further comprising retracting the guide wire in a proximal direction to cause the distal stop to abut against the filter element.

19. The method of claim 17 further comprising:
    providing a retrieval catheter having a recovery sock;
    advancing the retrieval catheter over the guide wire until the recovery sock covers a mouth of the filter element; and
    urging the retrieval catheter against the self-expanding struts of the filter element to cause the filter element to collapse.

* * * * *

Disclaimer

6,468,291 B2—Mark C. Bates, Charleston, WV; Michael Hogendijk, Palo Alto, CA. EMBOLI FILTRATION SYSTEM HAVING INTEGRAL STRUT ARRANGEMENT AND METHODS OF USE. Patent dated October 22, 2002. Disclaimer filed July 21, 2005, by the assignee, Baff LLC.

Hereby disclaims all claims of said patent.

*(Official Gazette, October 18, 2005)*

Disclaimer

6,468,291 B2—Mark C. Bates, Charleston, WV; Michael Hogendijk, Palo Alto, CA. EMBOLI FILTRATION SYSTEM HAVING INTEGRAL STRUT ARRANGEMENT AND METHODS OF USE. Patent dated October 22, 2002. Disclaimer filed July 21, 2005, by the assignee, Baff LLC.

Hereby disclaims all claims of said patent.

*(Official Gazette October 16, 2007)*